US012727805B2

(12) United States Patent
Kubo et al.

(10) Patent No.: US 12,727,805 B2
(45) Date of Patent: Sep. 8, 2026

(54) BIOELECTRODE

(71) Applicant: NOK CORPORATION, Tokyo (JP)

(72) Inventors: Masayuki Kubo, Fujisawa (JP); Takahiro Hayashi, Fujisawa (JP)

(73) Assignee: NOK CORPORATION (JP)

( * ) Notice: Subject to any disclaimer, the term of this patent is extended or adjusted under 35 U.S.C. 154(b) by 674 days.

(21) Appl. No.: 17/924,000

(22) PCT Filed: Jun. 7, 2021

(86) PCT No.: PCT/JP2021/021544
§ 371 (c)(1),
(2) Date: Nov. 8, 2022

(87) PCT Pub. No.: WO2022/004282
PCT Pub. Date: Jan. 6, 2022

(65) Prior Publication Data

US 2023/0270364 A1 Aug. 31, 2023

(30) Foreign Application Priority Data

Jul. 3, 2020 (JP) ................................ 2020-115673

(51) Int. Cl.
*A61B 5/251* (2021.01)
*A61B 5/263* (2021.01)
*A61B 5/291* (2021.01)

(52) U.S. Cl.
CPC .............. *A61B 5/251* (2021.01); *A61B 5/263* (2021.01); *A61B 5/291* (2021.01)

(58) Field of Classification Search
CPC .......... A61B 5/251; A61B 5/263; A61B 5/291
See application file for complete search history.

(56) References Cited

U.S. PATENT DOCUMENTS

2004/0138370 A1 7/2004 Higuchi et al.
2010/0025100 A1 2/2010 Hamano et al.
(Continued)

FOREIGN PATENT DOCUMENTS

JP H10-087897 A 4/1998
JP 2003-232130 A 8/2003
(Continued)

OTHER PUBLICATIONS

International Search Report (English and Japanese) issued in PCT/JP2021/021544, mailed Jul. 20, 2021; ISA/JP (5 pages).

*Primary Examiner* — Jennifer Pitrak McDonald
*Assistant Examiner* — Shreya Anjaria
(74) *Attorney, Agent, or Firm* — Harness, Dickey & Pierce, P.L.C.

(57) ABSTRACT

A bioelectrode is provided that can make it easy to maintain an electrode shape and suppress a burden on a subject of measurement. A bioelectrode includes a support member, an electrode member, and a connector. The electrode member has a supported section. The supported section has a supported surface and an electrode formation surface that face in opposite directions from each other. A plurality of electrode protrusions are provided on the electrode formation surface. The electrode member is formed of conductive rubber. The electrode protrusions each have a base end and a tip. The conductive rubber of the base end is harder than the conductive rubber of the tip.

6 Claims, 12 Drawing Sheets

(56) References Cited

U.S. PATENT DOCUMENTS

| | | | | |
|---|---|---|---|---|
| 2016/0143554 | A1* | 5/2016 | Lim | A61B 5/6803 600/386 |
| 2018/0020936 | A1* | 1/2018 | Kwon | H01B 5/14 600/388 |
| 2019/0239807 | A1 | 8/2019 | Watson et al. | |
| 2020/0029897 | A1* | 1/2020 | Takahashi | A61B 5/6801 |
| 2020/0237249 | A1* | 7/2020 | Gunasekar | A61B 5/6803 |
| 2021/0000371 | A1 | 1/2021 | Yoshitomi et al. | |
| 2021/0345927 | A1* | 11/2021 | Kitazoe | A61B 5/291 |

FOREIGN PATENT DOCUMENTS

| | | | | | |
|---|---|---|---|---|---|
| JP | 2013111361 | A | * | 6/2013 | A61B 5/0478 |
| JP | 2017-074369 | A | | 4/2017 | |
| JP | 2018-102964 | A | | 7/2018 | |
| JP | 2018-175288 | A | | 11/2018 | |
| KR | 200322161 | Y1 | | 8/2003 | |
| KR | 200437863 | Y1 | | 1/2008 | |
| WO | 2020-080396 | A1 | | 4/2020 | |
| WO | 2020-085034 | A1 | | 4/2020 | |
| WO | WO-2021254601 | A1 | * | 12/2021 | |

* cited by examiner

SECTION M1-M1

FIG. 16
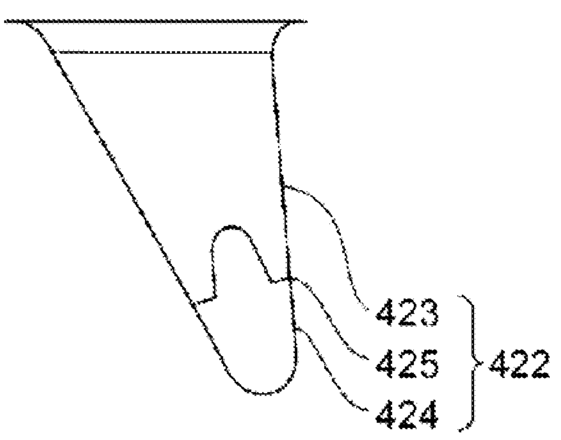
FIG. 17
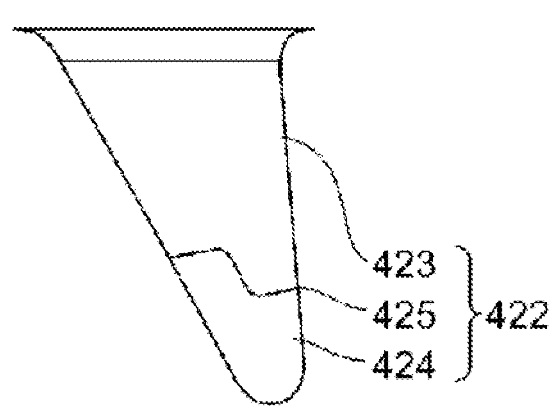
FIG. 18
| | MATERIAL USED | TIP | BASE END |
|---|---|---|---|
| | | MATERIAL E1 | MATERIAL E2 |
| BINDER | SILICONE RUBBER | 100 | 100 |
| SILVER POWDER | FIRST SILVER POWDER | 150 | 200 |
| | SECOND SILVER POWDER | 150 | 200 |
| DISPERSANT | FIRST DISPERSANT | 10 | 10 |
| | SECOND DISPERSANT | 10 | 10 |
(UNIT: PARTS BY WEIGHT)

BIOELECTRODE

CROSS REFERENCE TO RELATED APPLICATIONS

This application is a U.S. National Phase Application under 35 U.S.C. 371 of International Application No. PCT/JP2021/021544, filed on Jun. 7, 2021, which claims priority to Japanese Patent Application No. 2020-115673, filed on Jul. 3, 2020. The entire disclosures of the above applications are expressly incorporated by reference herein.

BACKGROUND

Technical Field

The present disclosure relates to a bioelectrode.

Background Art

An electrode for EEG measurement that has a plurality of comb teeth is described in, for example, Japanese Unexamined Patent Application Publication No. 2017-074369. The plurality of comb teeth are formed of a resin material as an example. The tip surfaces of the comb teeth are electrically conductive. By bringing the tip surfaces of the comb teeth into contact with a subject of measurement, the comb teeth can serve as electrodes. The subject of measurement is, for example, a scalp.

In addition, for example, Japanese Unexamined Patent Application Publication No. 2013-111361 describes a bioelectrode having tips with high hardness (being made of a metal). Further, Japanese Unexamined Patent Application Publication No. 2018-175288 describes a bioelectrode in which base ends are formed of a flexible material, thereby making it easy for the electrode to be easily inclined.

A bioelectrode is pressed against a subject of measurement when used. Even after the bioelectrode is repeatedly used, it is desired to maintain electrode protrusions as close to their initial shapes as possible. At the same time, it is desired to suppress the burden on a subject of measurement as much as possible when the electrode protrusions are brought into contact with the subject of measurement. Conventionally, there has been no technology that effectively satisfies both of these needs, and there has been a demand for further improvements in bioelectrodes.

The present disclosure provides a bioelectrode that can easily maintain the electrode shape thereof and suppress the burden on a subject of measurement.

SUMMARY

One aspect of the bioelectrode includes an electrode protrusion which has a base end and a tip connected to the base end and is constructed of conductive rubber, wherein the conductive rubber of the base end is harder than the conductive rubber of the tip.

Effect

The base end is harder than the tip, thus making it possible to easily maintain the electrode shape while simultaneously suppressing the burden on a subject of measurement by the soft tip.

BRIEF DESCRIPTION OF THE DRAWINGS

FIG. 16 is a front view illustrating the configuration of an electrode protrusion of another modified example;

FIG. 17 is a front view illustrating the configuration of an electrode protrusion of yet another modified example;

FIG. 18 is a table describing the materials of a bioelectrode of an example.

DETAILED DESCRIPTION

Figure 1:
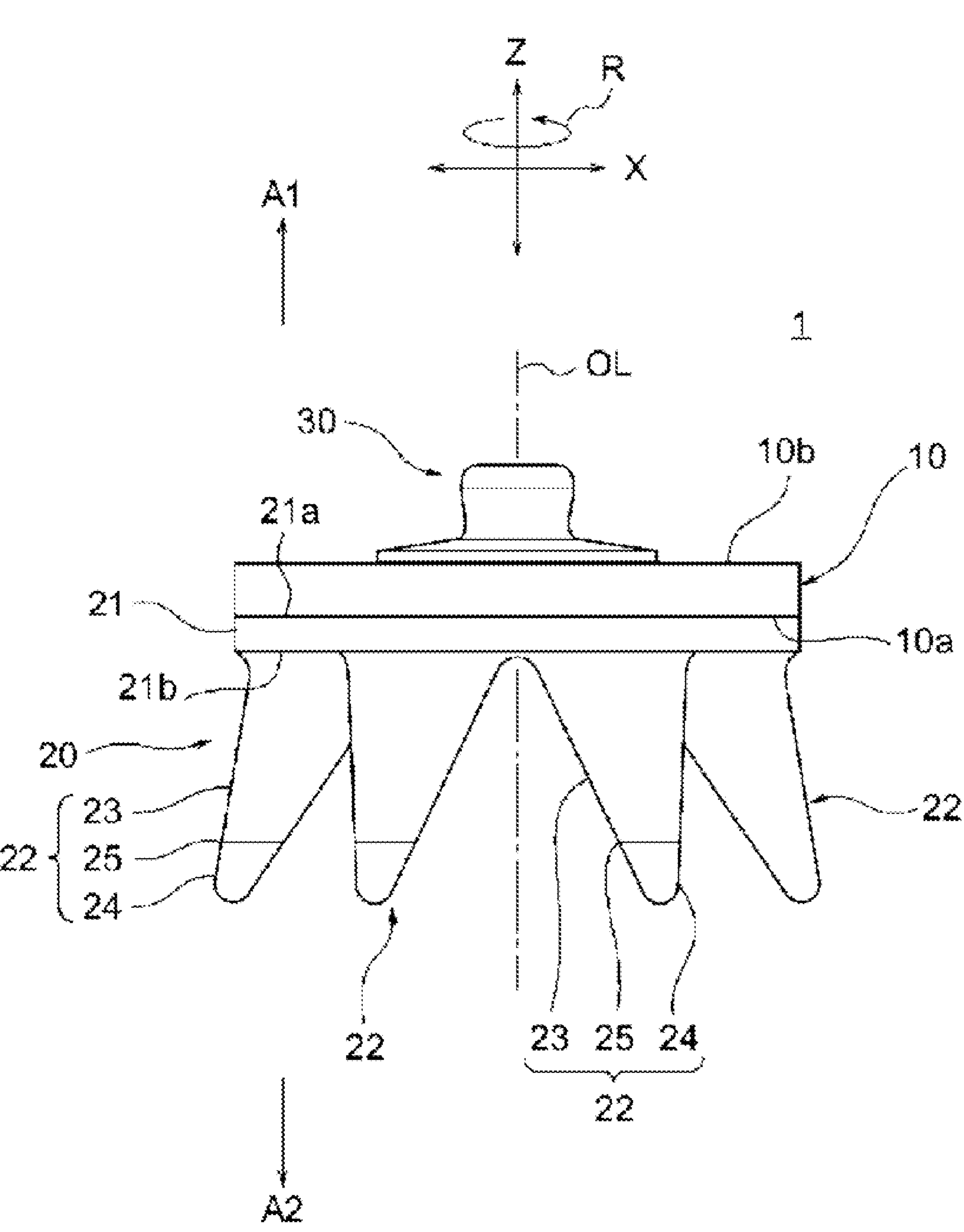
FIG. 1 is a front view illustrating the configuration of a bioelectrode of an embodiment.

FIG. 1 is a front view illustrating the configuration of a bioelectrode 1 of an embodiment. The bioelectrode 1 of the embodiment includes a support member 10, an electrode member 20, and a connector 30. The support member 10 is, for example, a plate-shaped member, and specifically a disc-shaped member. The support member 10 has a support surface 10*a*, which supports the electrode member 20, and a back surface 10*b* on the opposite from the support surface 10*a*.

The electrode member 20 has a supported section 21. The supported section 21 has a supported surface 21*a* and an electrode formation surface 21*b*, which face in opposite directions from each other. The supported surface 21*a* is fixed to the support surface 10*a*. A plurality of electrode protrusions 22 are provided on the electrode formation surface 21*b*. The connector 30 extends, penetrating the support member 10, and connects to the electrode member 20. The electrode member 20 can be electrically connected to an external measurement device or the like through the connector 30.

Figure 2:
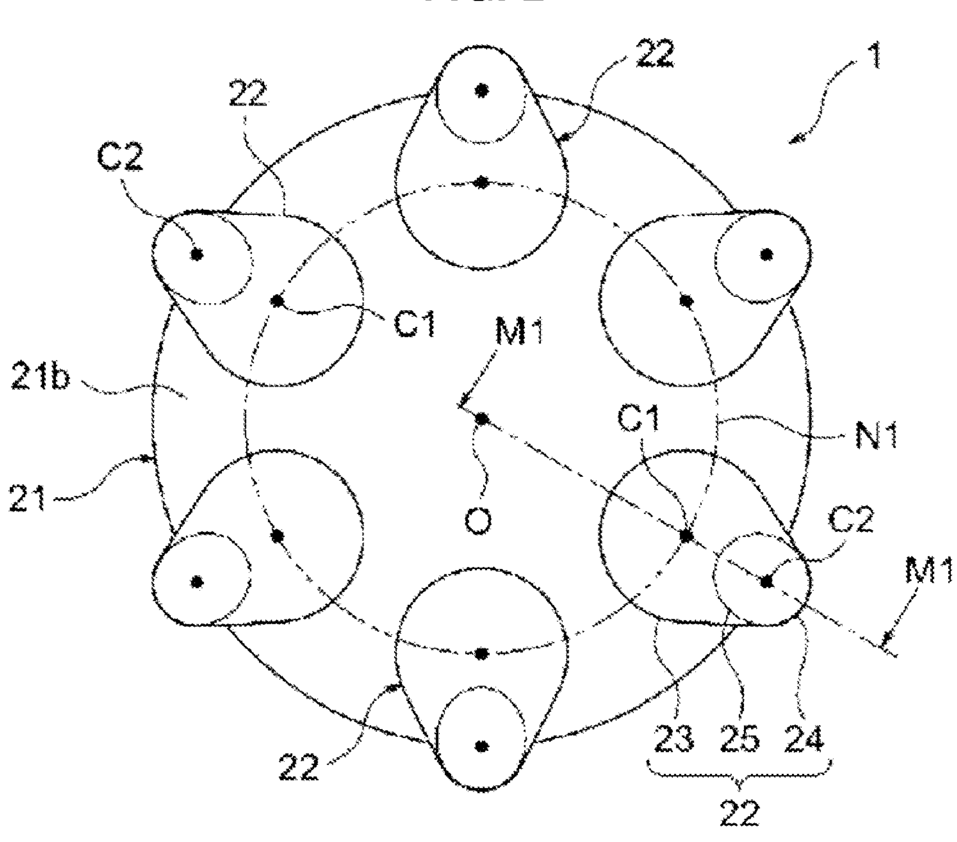
FIG. 2 is a bottom view illustrating the configuration of the bioelectrode of the embodiment.

FIG. 2 is a bottom view of the bioelectrode 1 of FIG. 1. At the center of the circular electrode formation surface 21*b*, "placement central point O" is illustrated. Six, for example, electrode protrusions 22 are circularly placed, surrounding the placement central point O.

Several drawings including FIG. 1 illustrate a main central axis OL, an axial direction Z, a radial direction X, and a circumferential direction R. These directions are defined for convenience in describing the embodiment. The "main central axis OL" is the central axis of the bioelectrode 1. The main central axis OL is a perpendicular to the electrode formation surface 21*b* passing through the placement central point O.

The axial direction Z and the main central axis OL are parallel. The radial direction X is a direction orthogonal to the axial direction Z. The radial direction X is further divided to a direction toward an outer diameter and a direction toward an inner diameter. The direction toward the outer diameter is a direction away from the main central axis OL. The direction toward the inner diameter is a direction approaching the main central axis OL. The circumferential direction R is a direction of rotation about the main central axis OL. A direction A1 in FIG. 1 denotes "the connector direction" of the bioelectrode 1, and a direction A2 denotes "the pressing direction" of the bioelectrode 1.

The support member 10 is formed of an electrically insulating material. The electrically insulating material may be, for example, silicone rubber, or any other hard resin materials. A through hole that passes through the support member 10 in the thickness direction is formed at the center of the support member 10. The connector 30 is passed through the through hole.

The electrode member 20 is formed of conductive rubber. The electrode member 20 has the supported section 21 and the plurality of electrode protrusions 22. Each of the electrode protrusions 22 has a base end 23 and a tip 24. The base end 23 is connected to the supported section 21. The tip 24 is connected to an end of the base end 23. The plurality of electrode protrusions 22 protrude from the supported section 21 to the opposite from the support member 10.

The connector 30 of the embodiment electrically connects the electrode member 20 to an external measurement device. A part of the connector 30 is embedded in the supported section 21. The connector 30 penetrates the support member 10 and is exposed on the back surface 10*b* of the support member 10. The connector 30 has no restrictions on the specific structure thereof, and the connector 30 may be a snap button type connector, and may be made of a metal such as stainless steel.

FIG. 2 illustrates a virtual circle N1 having the placement central point O as the central point thereof on the electrode formation surface 21*b*. The plurality of electrode protrusions 22 are equidistantly placed along the circumferential direction R on the virtual circle N1. FIG. 2 illustrates a cross sectional center C1 of the base end 23 and a cross sectional center C2 of the tip 24. The "cross section" of the electrode protrusion 22 is a cut surface obtained by cutting the electrode protrusion 22 along a plane parallel to the radial direction X in FIG. 1.

Each of the plurality of electrode protrusions 22 has a circular cross section and gradually decreases in diameter from the base end 23 toward the tip 24. Each of the plurality of electrode protrusions 22 is constructed such that the cross sectional area thereof gradually decreases from the base end 23 toward the tip 24 (i.e., away from the electrode formation surface 21*b*). The cross sectional center C1 of the base end 23 is positioned on the virtual circle N1. The cross sectional center C2 of the tip 24 is positioned radially outward relative to the cross sectional center C1. As an example, the tip 24 protrudes outward beyond the electrode formation surface 21*b*.

Figure 3:
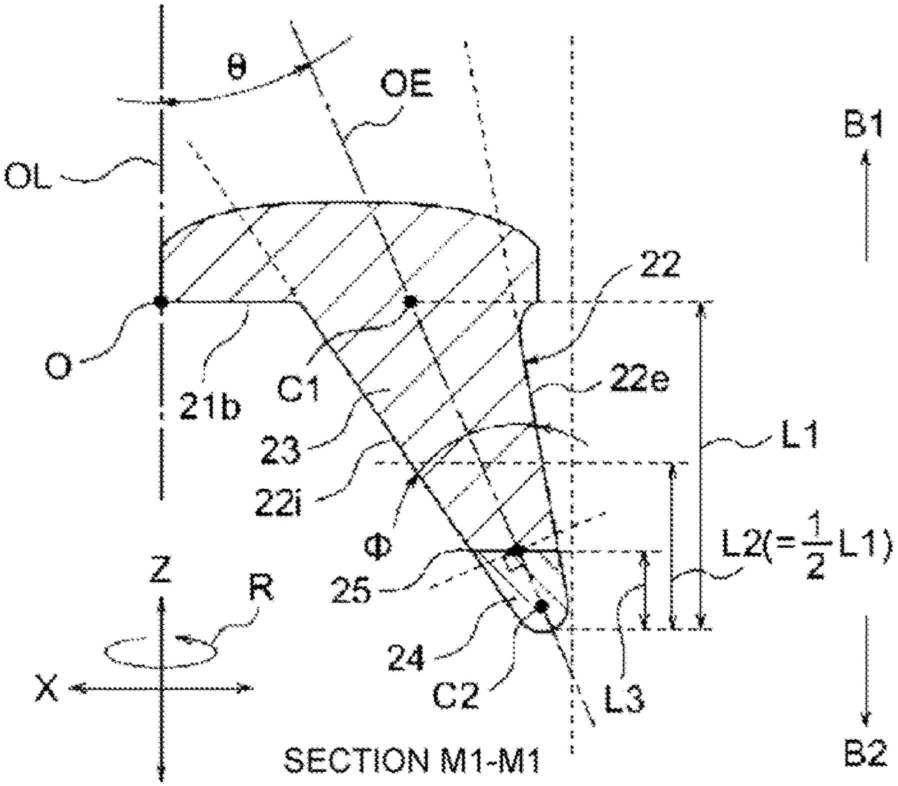
FIG. 3 is a sectional view illustrating the configuration of an electrode protrusion in the bioelectrode of the embodiment.

FIG. 3 is a sectional view of the electrode protrusion 22 along line M1-M1 in FIG. 2. FIG. 3 is also a longitudinal sectional view obtained by cutting the electrode protrusion 22 along a virtual plane that includes the main central axis OL. Each of the plurality of electrode protrusions 22 has the cross sectional shape of FIG. 3. FIG. 3 illustrates a virtual straight line OE connecting the cross sectional center C1 of the base end 23 and the cross sectional center C2 of the tip 24. The virtual straight line OE is also referred to as the "electrode axis OE" for convenience. So to speak, the virtual straight line OE corresponds to the central axis of the electrode protrusion 22. FIG. 3 illustrates arrows representing a base end direction B1 and a tip direction B2 of the electrode protrusion 22.

FIG. 3 illustrates several design parameters for explaining the shape of the electrode protrusion 22. The design parameters include an inclination angle θ, a taper angle q, and dimensions L1, L2 and L3. The dimensions L1, L2 and L3 are the total height L1 of the electrode protrusion 22 with reference to the electrode formation surface 21*b*, the half value L2 of the dimension L1, and the height dimension L3 of the tip 24, respectively.

The electrode axis OE and the main central axis OL form the inclination angle θ. Each of the electrode protrusions 22 also inclines so as to have the inclination angle θ relative to the main central axis OL. As illustrated in FIG. 2, the tip 24 expands toward the outer diameter with reference to the placement central point O.

The electrode protrusion 22 has an oblique conical shape with a rounded apex. In FIG. 3, of the side peripheral surfaces of the electrode protrusion 22, the surface closer to the inner diameter, i.e., the surface closer to the main central axis OL, is referred to also as an inner peripheral side surface 22*i*. In FIG. 3, of the side peripheral surfaces of the electrode protrusions 22, the surface closer to the outer diameter, i.e., the surface farther from the main central axis OL is referred to also as an outer peripheral side surface 22*e*. In the sectional view of FIG. 3, the outer peripheral side surface 22*e* is not parallel to the main central axis OL but has a certain degree of inclination relative thereto. The inclination angle of the outer peripheral side surface 22*e* relative to the main central axis OL is smaller than the inclination angle θ.

The height dimension L3 of the tip 24 is smaller than the dimension L2. This enables the base end 23 to occupy a larger proportion in the electrode protrusion 22, thus enhancing the shape retention of the electrode protrusion 22.

An interface 25 exists between the base end 23 and the tip 24. The interface 25 is parallel to the radial direction X and parallel to the electrode formation surface 21*b*. The interface 25 corresponds to a cross section obtained by cutting the boundary between the base end 23 and the tip 24. In the embodiment, the interface 25 obliquely intersects with the electrode axis OE. The normal of the interface 25 and the electrode axis OE form an angle that is larger than zero degrees.

The taper angle q of the electrode protrusion 22 is arbitrarily set within a range of greater than 0 degrees and less than 90 degrees. In the embodiment, as an example, the base end 23 and the tip 24 have the same taper angle q. The base end 23 and the tip 24 smoothly connect without a step at the interface 25.

Hereinafter, the materials of the embodiment will be described. The base end 23 and the tip 24 are each constructed of conductive rubber. The conductive rubber of the embodiment is specifically conductive silicone rubber containing silicone rubber and conductive particles. The silicone rubber may be, for example, a room temperature curing liquid silicone rubber. The room temperature curing liquid silicone rubber is in a liquid or paste form before curing, and the curing reaction progresses at 20° C. to 100° C. to form a rubber elastic body. In addition, reinforcing materials, fillers, various additives, and the like may be contained as appropriate.

The conductive particles may be, for example, metal particles. The metal particles may be, for example, silver particles. The silver particles may contain agglomerated particles (agglomerates) in which a plurality of silver particles (primary particles) agglomerate, may contain flaky silver particles, or may contain both of these. The conductive particles may be other metal particles, conductive carbon-based material particles, or the like. Other metal particles may be copper particles, gold particles, aluminum particles or nickel particles. Carbon-based material particles may be carbon black, graphite, carbon nanotubes, or the like. The carbon black may be ketjen black or acetylene black.

The conductive rubber of the base end 23 is harder than the conductive rubber of the tip 24. As an example of the means for creating the difference in hardness, the amount of the conductive particles of the base end 23 is set to be greater than the amount of the conductive particles of the tip 24 in the embodiment. The conductive rubber tends to become harder as the amount of conductive particles added to a binder such as the above-described silicone rubber is increased. This tendency is used in the embodiment.

In the embodiment, the material for constructing the tip 24 will be referred to as the "first material" for convenience, and the material for constructing the base end 23 will be referred to as the "second material" for convenience. The second material contains more conductive particles than the first material.

The first material for constructing the tip 24 may be as flexible as possible. However, in the first material, the total amount of conductive particles may be three times or more the amount of a binder thereby to ensure good conductivity. On the other hand, the second material for constructing the base end 23 may be as hard as possible. However, in the second material, the total amount of conductive particles may be four times or less the amount of a binder thereby to ensure fluidity.

Here, in the first material of the tip 24, the total amount (parts by weight) of the conductive particles is denoted as "R1" for convenience. In the second material of the base end 23, the total amount (parts by weight) of the conductive particles is denoted as "R2" for convenience. Both the conductivity and the fluidity described above may be ensured by blending the materials so as to satisfy, for example, the following conditional expression (1).

$$300 \leq R_1 < R_2 \leq 400 \quad (1)$$

When using the bioelectrode 1, the tips 24 of the plurality of electrode protrusions 22 are brought into contact with a part to be measured. The part to be measured is, for example, the body (skin) of a subject. In this condition, the biosignals of the subject are detected through the connector 30. The bioelectrode 1 detects, for example, brain waves or other biosignals other than brain waves.

The electrode member 20 is electrically connected to a measurement device (not illustrated) through the connector 30. The measurement device is not particularly limited, and may be, for example, an EEG measurement device, a wearable information device, or a health monitoring device.

In the bioelectrode 1 according to the embodiment described above, the burden on a part to be measured can be reduced by the soft tips 24, and the base ends 23, which are harder than the tips 24, make it easy to maintain the electrode shape.

More specifically, when the bioelectrode 1 is repeatedly pressed in the pressing direction A2 (that is, the tip direction B2) during use, the surface pressure may decrease due to permanent deformation (plastic deformation) or the like. It is desired to maintain the initial shape of the electrode protrusions 22 as much as possible. On the other hand, it is desired to suppress the burden on a part to be measured when the electrode protrusions 22 come in contact with a part to be measured. There is a need to achieve both improved shape retention characteristic and reduced measurement burden. In this regard, the base ends 23, which are harder than the tips 24, make it easy to maintain the electrode shape, while the flexibility of the tips 24 makes it possible to suppress the burden on a part to be measured.

In the embodiment, a difference in the hardness of the conductive rubber is created between the tips 24 and the base ends 23 by using different blending amounts of the conductive particles. Increasing the amount of the conductive particles has the advantage of improving rigidity as well as conductivity. Thus, the embodiment also has an excellent characteristic that makes it possible to achieve both rigidity and conductivity.

In the embodiment, the electrode protrusions 22 open radially outward with respect to the main central axis OL. Consequently, when the bioelectrode 1 is pressed against a part to be measured, the electrode protrusions 22 elastically deform, making it possible to stably cover a wide range of a measurement area.

In the embodiment, the hard conductive rubber ensures the conductivity and rigidity of the base ends 23. The embodiment is also characterized in that the base ends 23 are constructed of only conductive rubber, and no reinforcing metal insert components (e.g., metal bars) are provided inside the base ends 23.

In the embodiment, the interface 25 obliquely intersects with the electrode axis OE. The oblique intersection of the interface 25 and the electrode axis OE can make the area of the interface 25 larger than in the case where the two perpendicularly intersect.

The following will describe a first modified example to a third modified example of the embodiment with reference to FIG. 4 to FIG. 15.

Figure 4:
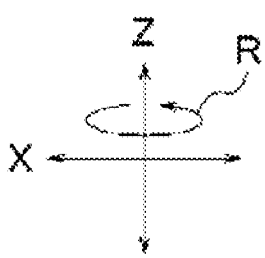
FIG. 4 is a front view illustrating the configuration of a bioelectrode in a first modified example.
Figure 4:
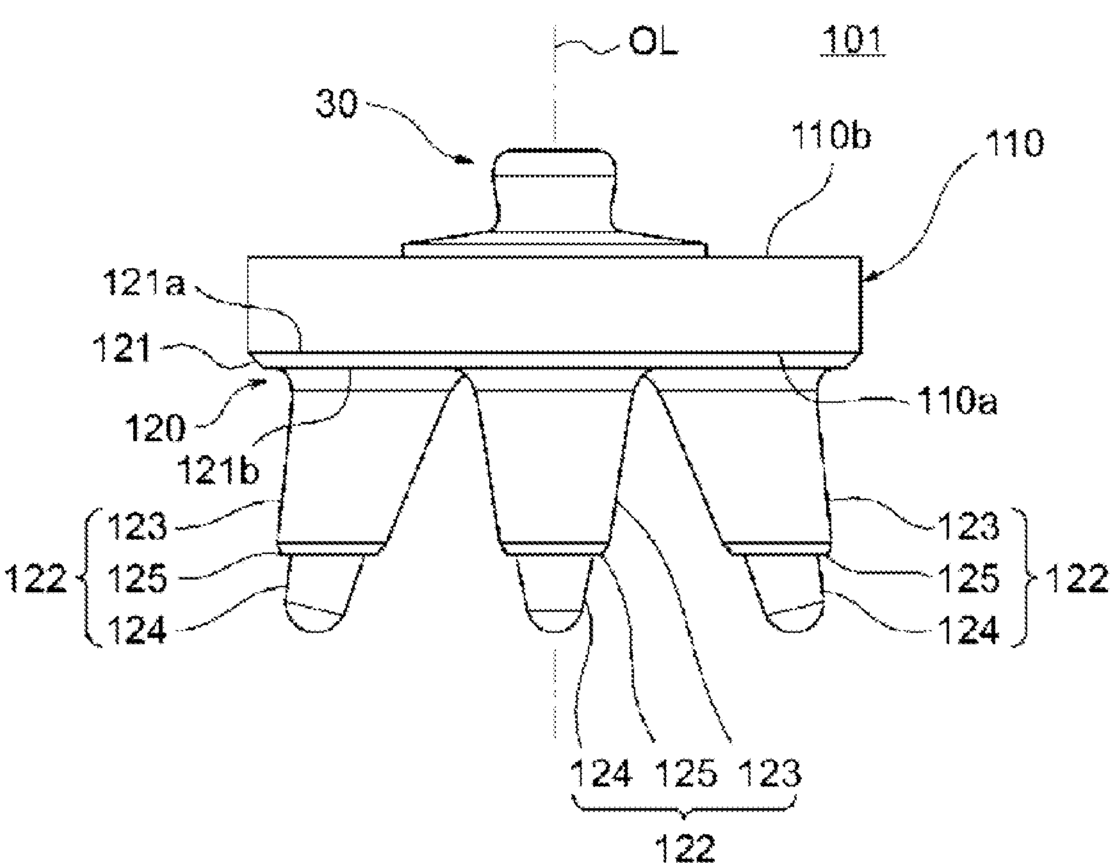
Figure 5:
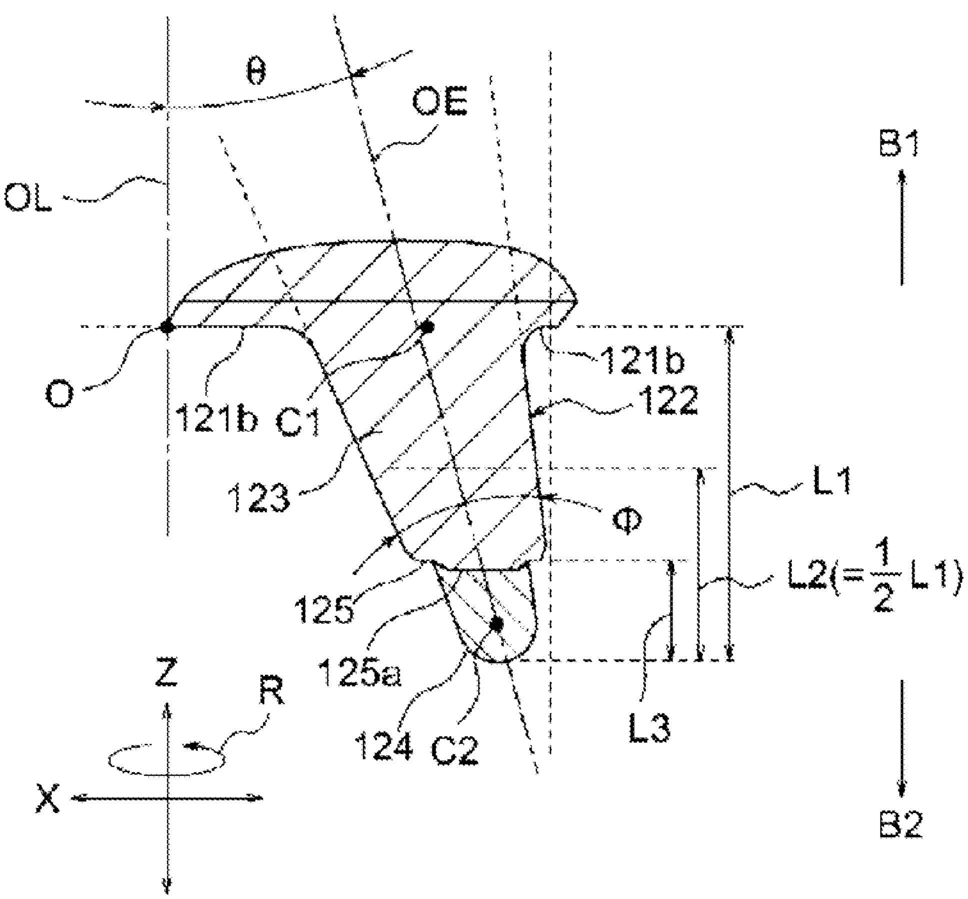
FIG. 5 is a sectional view of an electrode protrusion in the bioelectrode in the first modified example.
Figure 10:
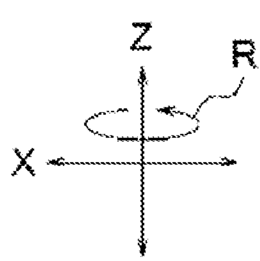
FIG. 10 is a front view illustrating the configuration of a bioelectrode in a second modified example.
Figure 10:
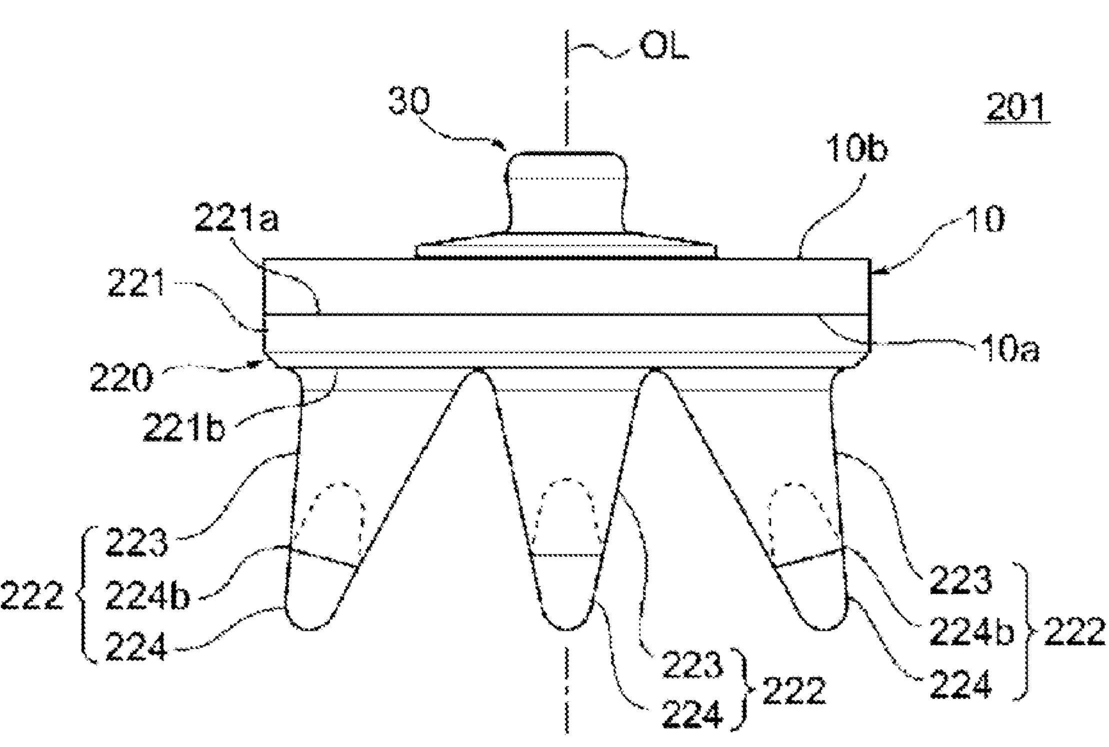
Figure 11:
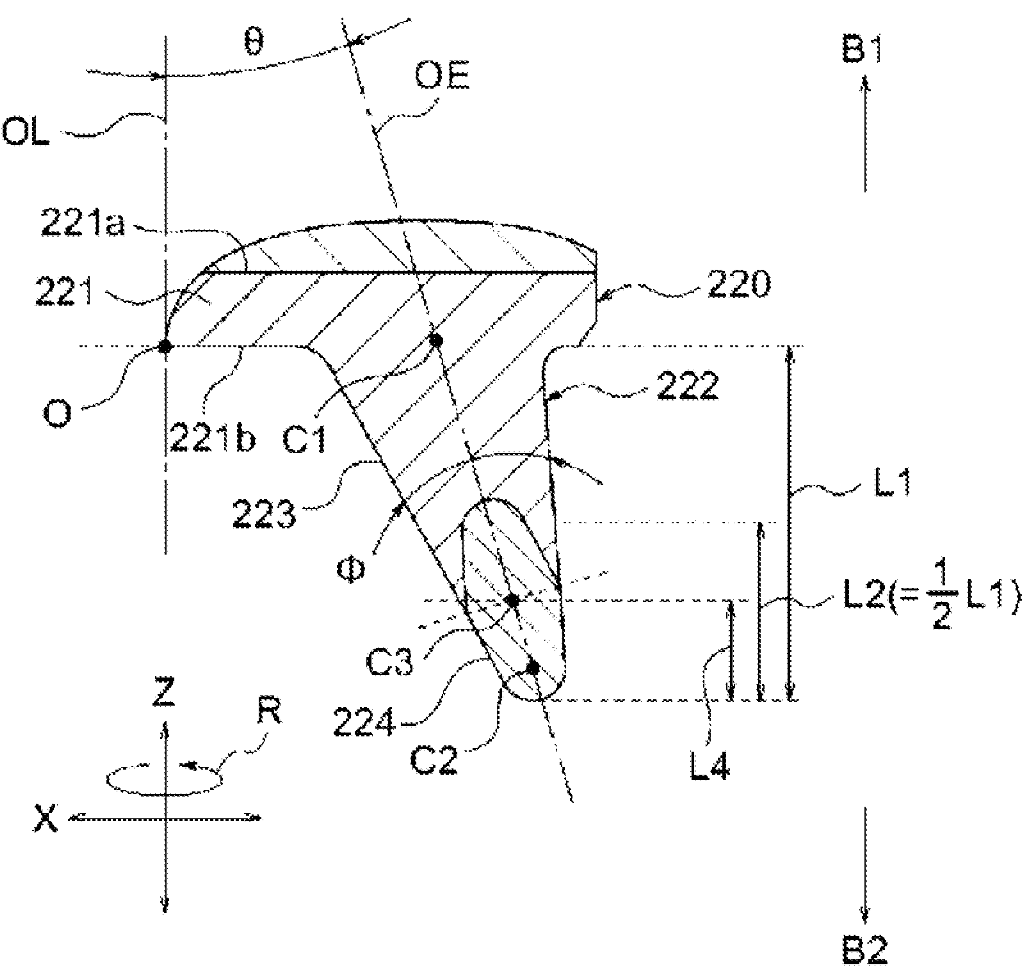
FIG. 11 is a sectional view illustrating the configuration of an electrode protrusion in the second modified example.
Figure 15:
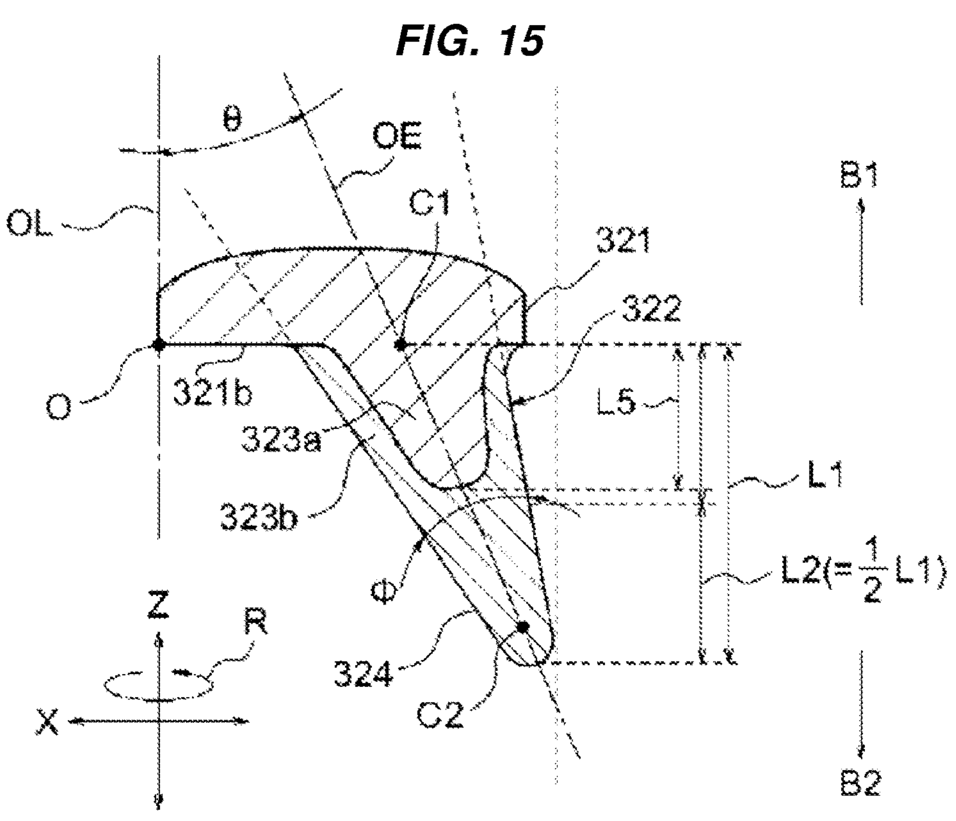
FIG. 15 is a sectional view illustrating the configuration of an electrode protrusion of a bioelectrode in a third modified example.

In summary, FIG. 4 and FIG. 10 are the front views of bioelectrodes 101 and 201 of the first modified example and the second modified example, respectively. FIG. 5, FIG. 11 and FIG. 15 are longitudinal sectional views of electrode protrusions 122, 222 and 322, respectively, of the first modified example to the third modified example. FIG. 5, FIG. 11 and FIG. 15 are longitudinal sectional views obtained by cutting each of the bioelectrodes of the modified examples by a virtual plane corresponding the line M1-M1 of FIG. 2, as with the bioelectrode 1. As with FIG. 3, the cross sectional centers C1 and C2, the electrode axis OE, and design parameters θ, φ, L1, L2, and L3 are entered in FIG. 5, FIG. 11 and FIG. 15.

Referring to FIG. 4 to FIG. 9, the first modified example will be described. FIG. 4 and FIG. 5 illustrate the structure of the bioelectrode 101 of the first modified example. The bioelectrode 101 has the same configuration as that of the bioelectrode 1 of the embodiment except that the electrode member 20 has been replaced by an electrode member 120.

The electrode member 120 has a supported section 121 and a plurality of electrode protrusions 122 extending from the supported section 121. The supported section 121 may have the same shape as that of the supported section 21. The supported section 121 includes a supported surface 121*a* and an electrode formation surface 121*b*, which face in opposite directions from each other. Each of the electrode protrusions 122 has a base end 123, a tip 124, and a connection end surface 125. The connection end surface 125 is an end surface of the base end 123 and also a surface connected to the tip 124. A protrusion 125*a* is provided at the center of the connection end surface 125.

The bioelectrode 101 of the first modified example has some characteristic configurations. One characteristic is a "protrusion" and a "recess" provided at the interface between the base end 123 and the tip 124. The "protrusion" and the "recess" fit with each other. In the first modified example, a protrusion 125*a* is provided on the base end 123, and the "recess" that receives the protrusion 125*a* is provided in the tip 124. More specifically, the tip 124 is placed over the protrusion 125*a*, and the protrusion 125*a* is buried in the tip 124. This makes it possible to increase the surface area where the tip 124 and the base end 123 are in contact with each other, thus improving the bonding force due to the increased contact area.

Another characteristic is that the peripheral edge of the connection end surface 125 is configured to have an annular step. The annular step is configured such that the tip 124 is slightly thinner than the base end 123. This makes the tip 124 easier to bend, thus further reducing the burden on a part to be measured.

As with the embodiment, the tip 124 is formed using the afore-described first material, and the base end 123 is formed using the afore-described second material.

Figure 6:
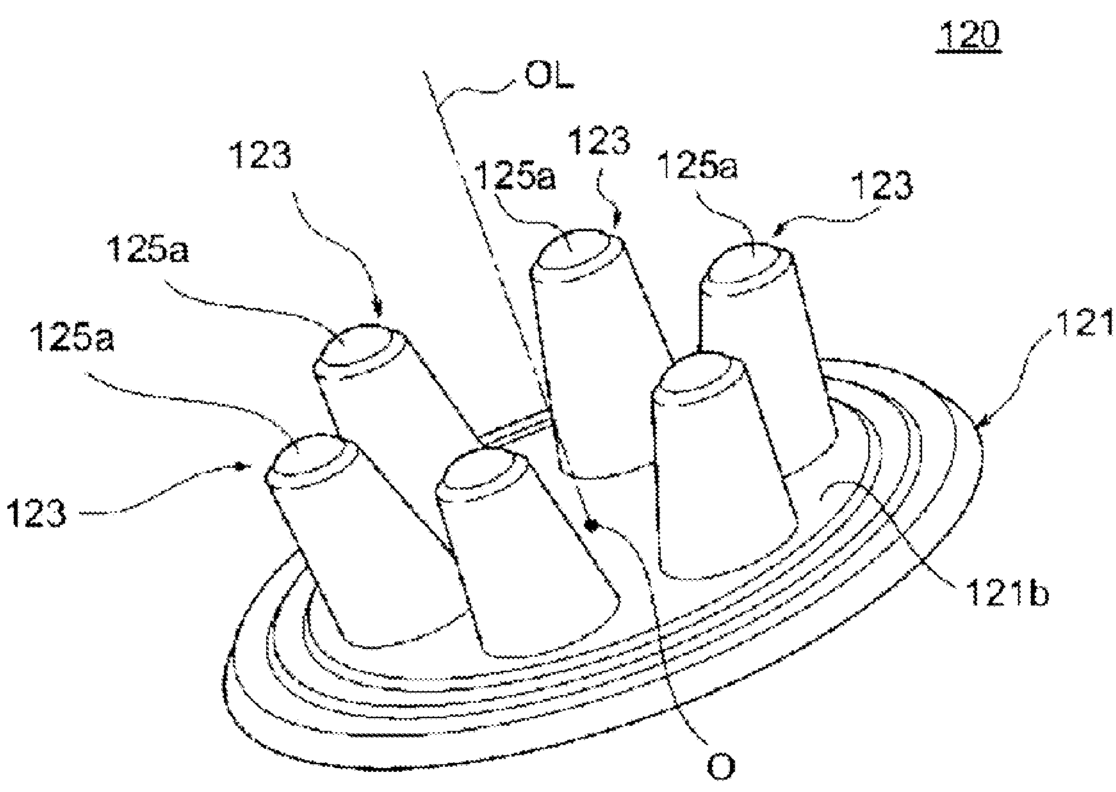
FIG. 6 is a bottom perspective view illustrating the intermediate product of the bioelectrode in the first modified example.
Figure 7:
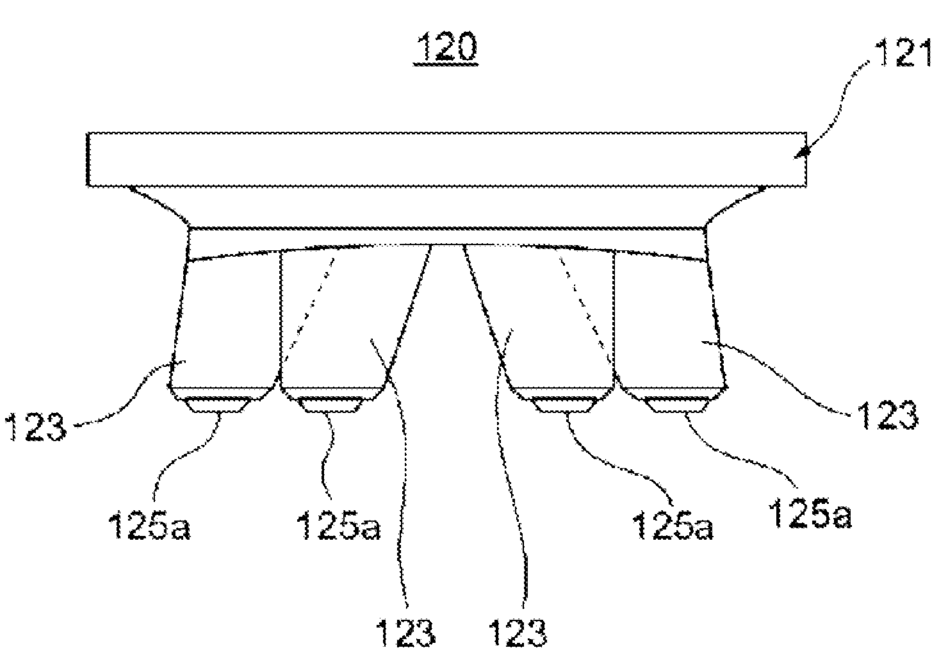
FIG. 7 is a front view illustrating the intermediate product of the bioelectrode in the first modified example.

An example of the manufacturing method of the first modified example will be described. First, the base end 123 is formed using conductive silicone rubber to make an intermediate product. FIG. 6 is a bottom perspective view illustrating the intermediate products of the bioelectrode 101, and FIG. 7 is a front view thereof. The base ends 123 that have been formed are set on a mold 150 (refer to FIG. 9) for forming the tips.

Figure 8:
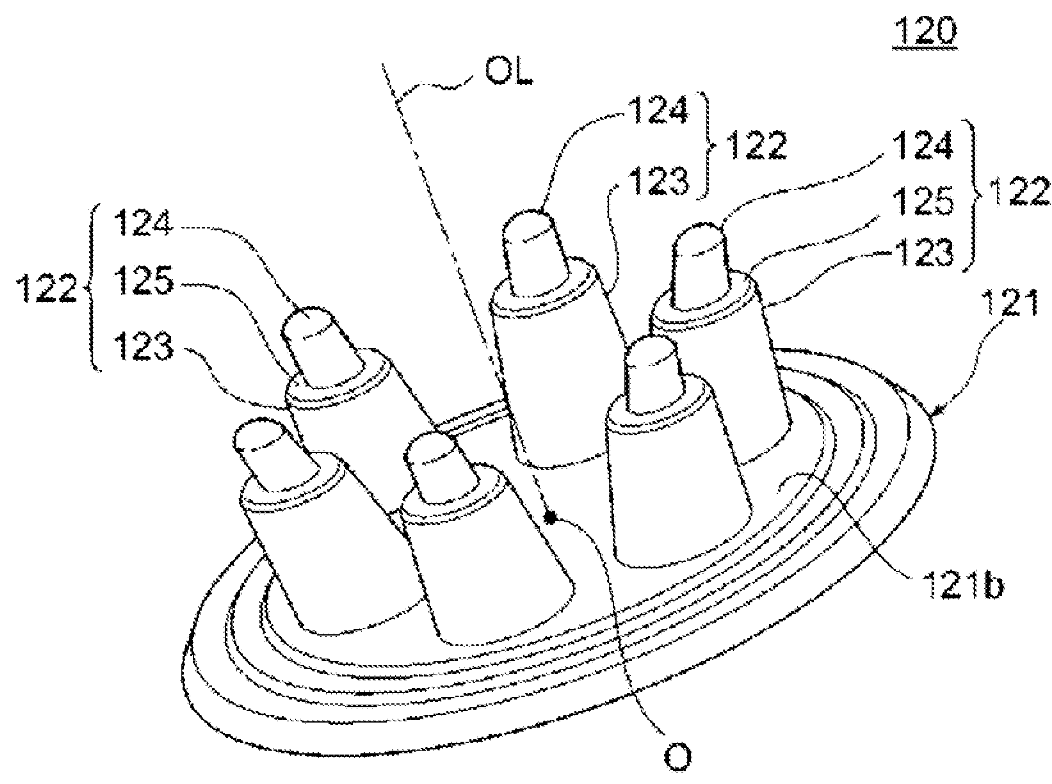
FIG. 8 is a bottom perspective view illustrating an electrode member constituting the bioelectrode in the first modified example.

Subsequently, the tips 124 are formed on the ends of the base ends 123 thereby to obtain a two-color molded product. FIG. 8 is a bottom perspective view of the electrode member 120 of the bioelectrode 101. In FIG. 6 and FIG. 8, the outer periphery of the supported section 121 is schematically illustrated slightly large, but the peripheral edge of the supported section 121 can be cut slightly smaller.

Figure 9:
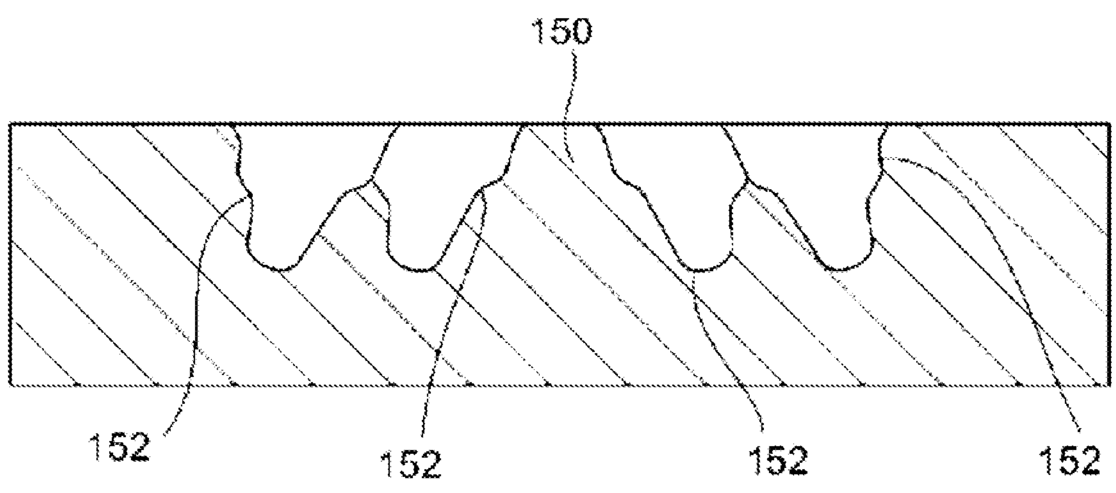
FIG. 9 is a sectional view of a mold for creating the tips of the bioelectrode in the first modified example.

FIG. 9 is a sectional view of the mold 150 for constructing the tips 124 of the bioelectrode 101. The annular steps of the connection end surfaces 125 can restrict the position (depth) of the insertion of the intermediate products of FIG. 6 and FIG. 7 when molding the tips 124. More specifically, the mold 150 has oblique conical hole portions 152 matching the shape of the electrode protrusions 122. Each of the oblique conical hole portions 152 is provided with a step corresponding to the annular step of the connection end surface 125. This step facilitates the positioning (determining the depth of) the intermediate product.

The two characteristics of the first modified example described above may be implemented independently from each other. As a modified example, the annular steps of the connection end surfaces 125 may be omitted while the protrusions 125*a* are provided. The omission of the annular steps is accomplished by modifying the shape of the oblique conical hole portions provided in the mold 150. In this modified example, oblique conical hole portions 152 for smoothly connecting the tips 124 and the base ends 123 are provided such that the tips 124 and the base ends 123 have the same taper angle. On the other hand, a modified example in which the protrusions 125*a* are omitted may be provided. In this case, the end surfaces of the base ends 123 are flat, and the tips 124 that are slightly thinner are connected to the flat end surfaces.

In the first modified example described above, the protrusions 125*a* fit in the recesses of the tips 124 at the interface between the base ends 123 and the tips 124. This ensures the contact surface area, leading to an improved bonding force.

In the above-described first modified example, the peripheral edges of the connection end surfaces 125 create the annular steps. The annular steps characteristically make the tips 124 slightly thinner than the base ends 123.

Referring to FIG. 10 to FIG. 14, a second modified example will be described. FIG. 10 and FIG. 11 illustrate the structure of a bioelectrode 201 of the second modified example. The bioelectrode 201 has the same configuration as that of the bioelectrode 1 of the embodiment except that the electrode member 20 has been replaced by an electrode member 220.

The electrode member 220 includes a supported section 221 and a plurality of electrode protrusions 222 extending from the supported section 221.

The shape of the supported section 221 may be the same as that of the supported section 21. The supported section 221 includes a supported surface 221*a* and an electrode formation surface 221*b*, which face in opposite directions from each other. Each of the electrode protrusions 222 has a base end 223 and a tip 224. FIG. 11 illustrates a cross sectional center C3 in the midsection of the tip 224.

A part of the tip 224 is buried in the base end 223, so that the surface area increases where the base end 223 and the tip 224 are in contact with each other. The increase in the contact area improves the bonding force.

Figure 12:
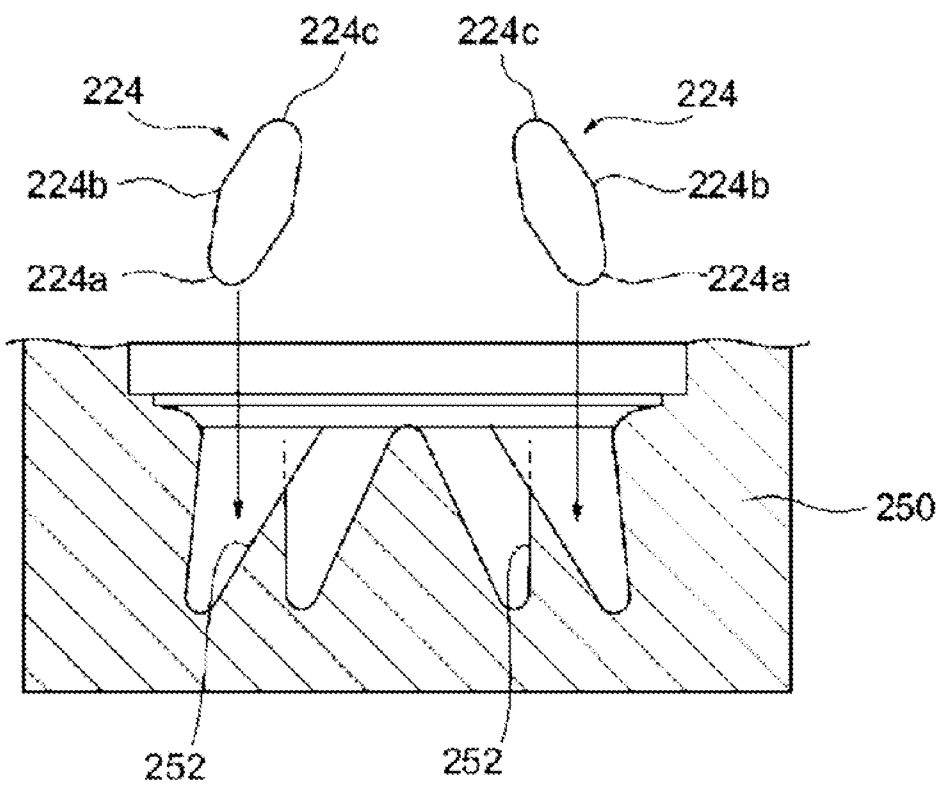
FIG. 12 is a diagram illustrating the manufacturing process of the bioelectrode in the second modified example.
Figure 13:
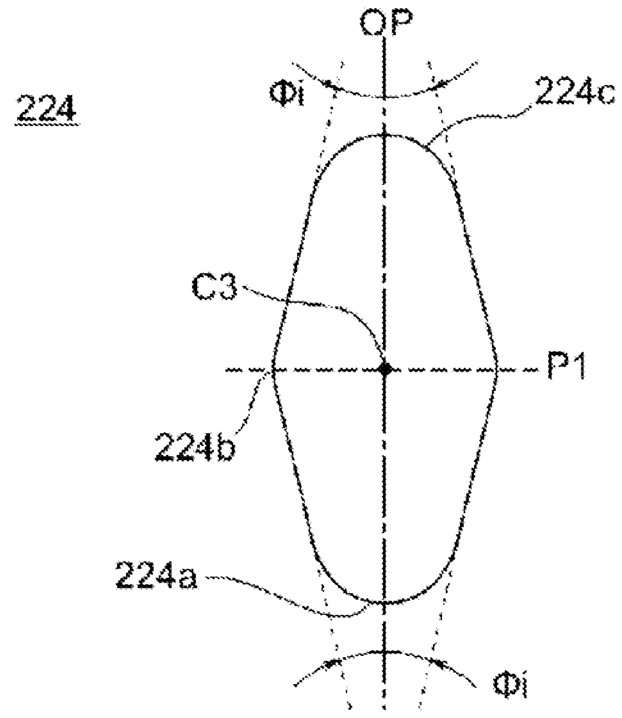
FIG. 13 is a front view of an insert component in the second modified example.

FIG. 12 is a diagram illustrating the manufacturing process of the bioelectrode 201. In the manufacturing method of the second modified example, the tips 224 are molded in advance as insert components. FIG. 13 is a front view illustrating an insert component of the second modified example of the embodiment. The material of the tips 224 is the afore-described "first material." Each of the tips 224 has a front end 224*a*, a midsection 224*b*, and a rear end 224*c* along a central axis OP thereof. The midsection 224*b* bulges out relative to both ends.

Figure 14:
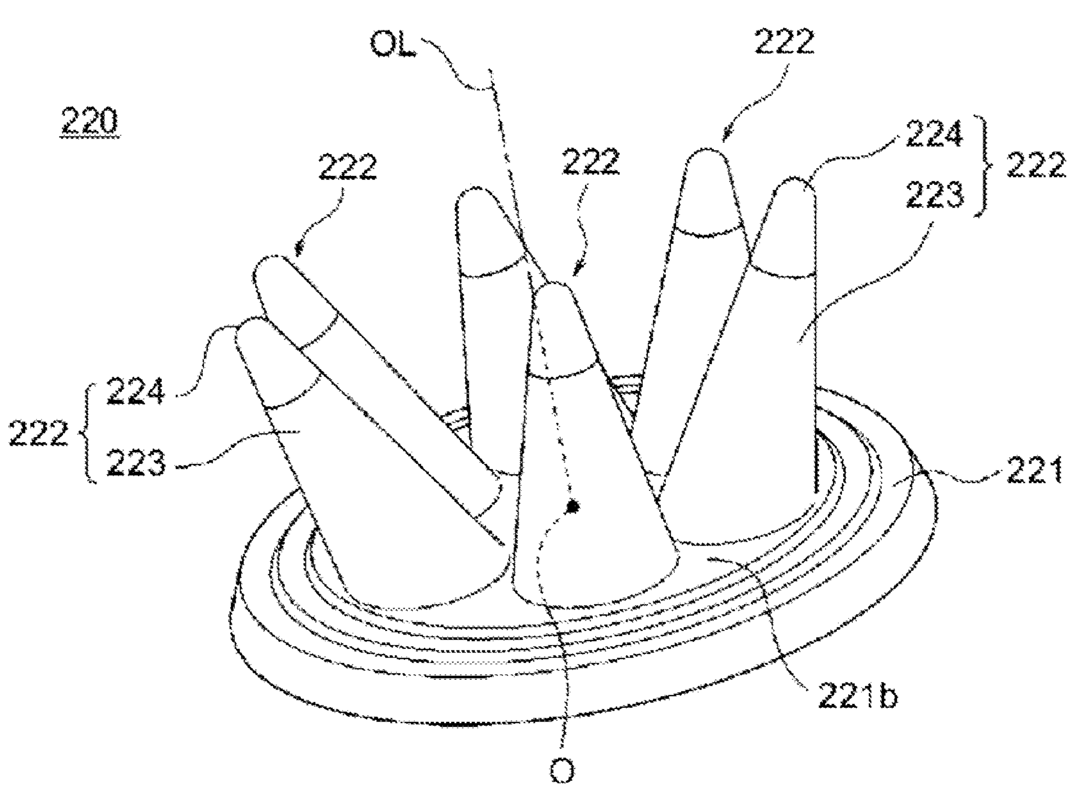
FIG. 14 is a bottom perspective view illustrating an electrode member of the bioelectrode in the second modified example.

FIG. 12 illustrates a mold 250 used for manufacturing the electrode member 220. The mold 250 has a plurality of oblique conical hole portions 252. The tips 224, which are insert components, are set in the oblique conical hole portions 252 as indicated by the arrows in FIG. 12. Subsequently, the afore-described "second material" is supplied into the mold 250, and the base ends 223 and the supported section 221 are formed so as to obtain the electrode member 220, which is a two-color molded product. FIG. 14 is a bottom perspective view illustrating the electrode member 220.

The bioelectrode 201 of the second modified example has some characteristic configurations. One characteristic is a "protrusion" and a "recess" provided at the interface between the base end 223 and the tip 224, and the "protrusion" and the "recess" fit with each other at the interface. In the second modified example, the rear end 224*c* in the tip 224 forms the "protrusion," and the "recess" receiving the rear end 224*c* is provided in the base end 223. In the structure of FIG. 10, as an example, exactly half of the tip 224 (i.e., up to the midsection 224*b*) is buried in the base end 223. This increases the surface area of resin bonding. The burying enables the base end 223 to stably hold the tip 224 when the tip 224 is subjected to a force. As a further modification, less than half of, or half or more of the tip 224 may be buried in the base end 223.

Another characteristic of the second modified example is that the tips 224 are insert components. Insert components provide manufacturing advantages. For example, the tips 224 can be formed in any shape and with any material independently of the manufacturing conditions imposed on the resin molding process of the base ends 223.

Yet another characteristic of the second modified example is that the tips 224 have various types of "symmetry" described below.

The "first symmetrical shape" of the tip 224 is a "mirror image symmetrical shape" when a cross section P1 of the midsection illustrated in FIG. 13 is used as a mirror plane. One of the advantages is improved workability during manufacturing. For example, if the tips 224 are insert components, the front ends 224*a* and the rear ends 224*c* may be reversed, thus reducing the burden on an operator.

The "second symmetrical shape" of the tip 224 is a rotationally symmetrical shape when the central axis OP in the length direction of the tip 224 (refer to FIG. 13) is used as the rotation axis. This rotationally symmetrical shape may be, for example, 1/2 rotationally symmetrical, 1/3 rotationally symmetrical, or n rotationally symmetrical. One of the advantages is that the workability of placing the tips 224 in a mold is improved if the tips 224 are insert components. Another advantage of having a rotationally symmetrical shape is that the bonding surface between the tip 224 and the base end 223 is also rotationally symmetrical, thus making it easy to achieve uniform bonding strength.

The "third symmetrical shape" of the tip 224 is a symmetrical shape tapered at both ends, and more specifically, the section along the central axis OP is rhombic. Both the front end 224*a* and the rear end 224*c* have the same taper angle $\varphi_i$. Consequently, the front end 224*a* and the rear end 224*c* are reversible, and the tip 224 is rotatable about the central axis thereof. Thus, there is no limitation on the setting direction relative to the mold 250, leading to improved workability.

The taper angle $\varphi_i$ does not have to be equal to the taper angle $\varphi$ of the base end 223. Alternatively, the magnitude relationship between the taper angle $\varphi_i$ and the taper angle $\varphi$ may be $\varphi_i<\varphi$ or $\varphi_i>\varphi$.

The tip 224 includes all of the first to the third symmetrical shapes described above. However, the tip 224 may be modified to have any one or two symmetrical shapes among these.

As an example, the tip 224 may be modified to have an asymmetrical shape. For example, the tip 224 may be modified into any shape that is non-mirror symmetrical with respect to the central cross section P1. As an example, the front end 224*a* may be an oblique cone, while the rear end 224*c* may be a cylinder, a prism, a truncated cone, or a truncated pyramid. As another example, the taper angle $\varphi_i$ of one of the front end 224*a* and the rear end 224*c* may be set to be larger than that of the other.

As a further modified example of the second modified example, the same structure as that of the tip 224 may be created using another manufacturing method that does not use insert components. For example, a "protrusion" may be provided on the bottom of each of the oblique conical hole portions 252 in the mold 250, and the base ends 223 may be formed by the oblique conical hole portions 252 with the protrusions. Thus, a "recess that is recessed toward the base end" can be provided in the end surface of the base end 223. A part of the tip 224 may be buried in the base end 223 by forming the tip 224 in the "recess that is recessed toward the base end."

As described above, in the second modified example, the rear end 224*c* of the tip 224 fits in the recess of the base end 223. Consequently, the contact surface area can be secured, resulting in an improved bonding force.

Referring to FIG. 15, a third modified example will be described. FIG. is a longitudinal sectional view of an electrode protrusion 322. The third modified example has the same structure as that of the embodiment (FIG. 1 and FIG. 2) except for the structure illustrated in FIG. 15. The base end of the third modified example has a double structure that includes a base end 323*a* (hereinafter referred to also as the inner base end 323*a*) and a base end 323*b* (hereinafter referred to also as the outer base end 323*b*). The inner base end 323*a* projects from an electrode formation surface 321*b* by a height L5. The outer base end 323*b* covers the inner base end 323*a* so as to bury the inner base end 323*a*.

The outer base end 323*b* continuously extends in an oblique conical shape in a tip direction B2, and the end thereof is a tip 324. The inner base end 323*a* and a supported section 321 are formed to be rigid by using the afore-described "second material." The entire outer base end 323*b* and the entire tip 324 are formed to be soft by using the afore-described "first material."

In the first modified example and the second modified example described above, the "protrusion" and the "recess" are provided at the interface between the base end 123 or 223 and the tip 124 or 224 such that the protrusion is buried in the recess (refer to the sectional view of each modified example). The embodiment is not limited to such shapes.

FIG. 16 and FIG. 17 are the front views of electrode protrusions 422 of other modified examples. For example, as one modified example, like an electrode protrusion 422 illustrated in the front view of FIG. 16, a base end 423 having a concave-shaped recess and a tip 424 having a convex-shaped protrusion may be constructed to fit with each other. In FIG. 16, an interface 425 appears on the outer surface of the electrode protrusion 422, and the convex and concave lines of the interface 425 are visible from outside. Further, in the present disclosure, "the protrusions" may include a "high step portion" and a "recess" may include a "low step portion." As an example of this case, the base end 423 and the tip 424 may be provided with a pair of steps that fit with each other without a gap, like the electrode protrusion 422 illustrated in the front view of FIG. 17. In the configuration of FIG. 17, as in FIG. 16, the convex and concave lines of the interface 425 appear on the outer surface of the electrode protrusion 422.

Still other modifications may be applied to the embodiment and the first to the third modified examples. Any one or a plurality of types of modifications may be selected from the following modification group and applied to the embodiment and the afore-described first to third modified examples.

The design parameters θ to L5 of the electrode protrusions 22 to 322 illustrated in FIG. 3, FIG. 5, FIG. 11 and FIG. 15 can be changed in various ways. For example, the inclination angle θ can be changed to any angle. As an example, the inclination angle θ may be set such that each of the electrode protrusions 22 to 322 vertically protrudes from the electrode formation surfaces 21*b* to 321*b*. In this case, the electrode axis OE of each of the electrode protrusions 22 is parallel to the main central axis OL and the axial direction Z.

A shape without the taper angle φ may be used. One or both of the base ends 23 to 323 and the tips 24 to 324 may be configured to have a uniform thickness without taper. Heights L3, L4 and L5 may be equal to or greater than a dimension L2. The tips 24 to 324 may be shorter than the base ends 23 to 323 or may be conversely longer, or may have the same length.

Of the changes in the afore-described design parameters θ, q, L3, L4, and L5, any one change, any two changes, or all three changes may be applied.

The thicknesses (i.e., the diameters of cross sections) of the tips 24 to 324 and the base ends 23 to 323 may be changed independently from each other. The tips 24 to 324 may be thicker than the base ends 23 to 323.

The basic shape of the bioelectrode of the present disclosure is not limited to the bioelectrodes 1, 101, and 201 of the embodiment and the modified examples thereof, and the characteristics of the present disclosure can be applied to various bioelectrode shapes. The method of placing each of the plurality of electrode protrusions 22 to 322 can be arbitrarily modified. The plurality of electrode protrusions 22 to 322 may be placed in a comb-shaped row (like a comb) rather than being limited to the circular pattern as in the embodiment. The number of electrode protrusions 22 to 322 may also be any number, for example, one. The overall shape of the electrode protrusions 22 to 322 is not necessarily limited to the oblique conical shape, and may be, for example, a thin pin shape, a bent pin shape, or, for example, a plate shape.

Example 1

The following will describe an example of a specific implementation of the bioelectrode 1 of the embodiment. However, the present disclosure is not limited by specific numerical values and product names, and the like described in this example.

FIG. 18 is a table describing the bioelectrode material components of the example. In the example, "Material E1" is applied as an example of the first material described above, and "Material E2" is applied as an example of the second material described above. The material E1 and the material E2 each contain 100 parts by weight of a binder. The binder is a liquid silicone rubber, and has a trade name of "KE-106" manufactured by Shin-Etsu Chemical Co., Ltd., for example, is used. The binder contains a curing agent. The curing agent used has a trade name of "CAT-RG" manufactured by Shin-Etsu Chemical Co., Ltd.

The material E1 contains a total of 300 parts by weight of silver powder (i.e., silver particles) per 100 parts by weight of the binder. The silver powder of the material E1 consists of 150 parts by weight of first silver powder and 150 parts by weight of second silver powder. The first silver powder has a trade name of "FA-2-3" and the second silver powder has a trade name of "G-35," both of which are manufactured by DOWA Electronics Materials Co., Ltd. The G-35 is mixed in advance with approximately 2 wt % of hydrophobic fumed silica (trade name "AEROSIL (registered trademark) R972" manufactured by NIPPON AEROSIL CO., LTD.) as an anti-agglomeration measure. The material E2 contains a total of 400 parts by weight of silver powder (silver particles) per 100 parts by weight of the binder. The silver powder of the material E2 consists of 200 parts by weight of the first silver powder and 200 parts by weight of the second silver powder.

The material E1 and the material E2 each contain 20 parts by weight of a dispersant. The dispersant of 20 parts by weight consists of a first dispersant of parts by weight and a second dispersant of 10 parts by weight. The first dispersant has a trade name of "KF-6015" and the second dispersant has a trade name of "KF-6106," both of which are manufactured by Shin-Etsu Chemical Co., Ltd.

An example of the manufacturing method of the example will be briefly described. In the following description, a connector 30 is attached to a support member 10 in advance. In the example, first, conductive rubber containing silicone rubber and metal particles is stirred. The conductive rubber may be in a liquid or paste form. The conductive rubber that has been stirred is injected into a mold for molding (cavity) having a plurality of oblique conical hole portions.

To mold the tips 24, the "material E1 (refer to FIG. 18)" is measured into the oblique conical hole portions of the mold, and defoaming and filling are performed by a self-rotating mixer. Subsequently, curing is performed at 150° C. for 2 minutes. Thereafter, the mold is cooled.

Next, the base ends 23 and the supported section 21 are formed. More specifically, after the mold is cooled, the "material E2 (refer to FIG. 18)" is further poured into the oblique conical hole portions of the mold. Subsequently, the assembly of the support member 10 and the connector 30 is placed on the conductive rubber in the mold, with the support surface 10*a* of the support member 10 facing downward. Thus, the support surface 10*a* of the support member 10 is placed, overlapping the supported surface 21*a*.

After setting the support member 10, defoaming and filling are performed. Further, curing is performed under a condition of 150° C. for 3 minutes. Subsequently, secondary vulcanization is performed at 150° C. for 30 minutes. Thus, the electrode member 20 made of conductive silicone rubber is obtained. Thereafter, the electrode member 20 is immersed in a 10% NaCl aqueous solution, and subjected to heat and pressure treatment under a condition of 121° C. and 0.1 MPa for 1 hour. An autoclave is used for the heat and pressure treatment.

Next, with the assembly of the support member 10 and the connector 30 in place, the conductive rubber formed in the shape of the electrode member 20 is cross-linked. This integrates the components. Thereafter, the bioelectrode 1 that has been integrated is removed from the mold (i.e., demolded).

Figure 19:
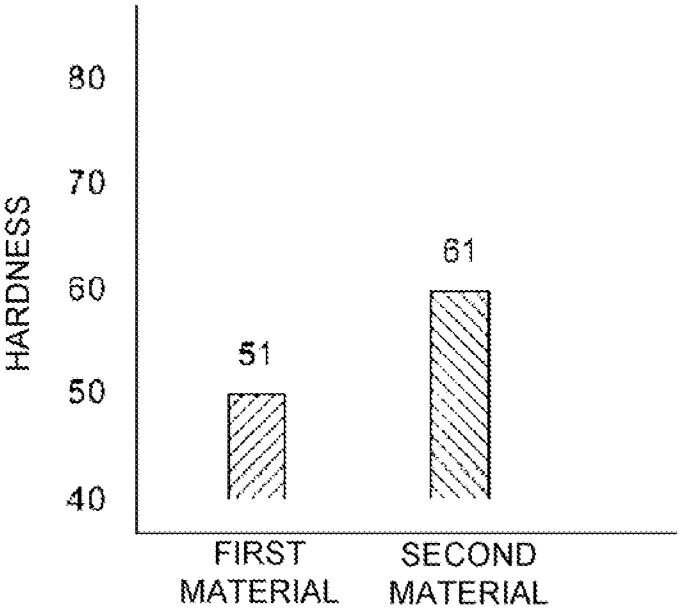
FIG. 19 is a graph illustrating the relationship between the amount of silver powder and hardness of the bioelectrode of the example.

FIG. 19 is a graph illustrating the relationship between the amount of silver powder and the hardness of the bioelectrode 1 of the example. The hardness in FIG. 19 is Shore A hardness. As illustrated in FIG. 19, in the example, when the amount of added silver powder is 150 parts by weight, the Shore A hardness is 51, and when the amount of added silver powder is 200 parts by weight, the Shore A hardness is 61. Since 61/51=1.196, in the example, it can be said that the Shore A hardness of the base end 23 is approximately 1.2 times that of the tip 24. As an example, the amount of added silver powder for the base end 23 may be greater than that for the tip 24 to an extent that the Shore A hardness is 1.2 times or more.

In the example, the silver powder (i.e., silver particles) is not limited as long as the silver powder can be dispersed in silicone rubber, which is the binder. For example, at least one of agglomerated silver powder and flaky silver powder may be used. Agglomerated silver powder is a three-dimensional agglomeration of a plurality of primary particles in a particle form, and the above trade name "G-35" is an example. Flaky silver powder has a scale shape. Both agglomerated silver powder and flaky silver powder may be added.

In order to obtain both flexibility and high conductivity, the amount of each of FA-2-3 and G-35 in the material E1 may be 1.5 times or more the amount of the binder. In this case, the total amount of silver powder may be 3.0 times or more the amount of the binder. On the other hand, in order to obtain both rigidity and fluidity, the amount of each of FA-2-3 and G-35 in the material E2 may be 2.0 times or less that of the binder. In this case, the total amount of silver powder may be 4.0 times or less the amount of the binder. FA-2-3 and G-35 to be added are not limited to the same amount, and one of these two may be added in a greater amount than the other.

The above-described examples include specific disclosure of at least material components, the trade names of materials, hardness, and manufacturing methods. The specific disclosure of the above-described examples may be applied to the bioelectrodes of the first to the third modified examples, or further modifications.

The invention claimed is:

1. A bioelectrode comprising:

an electrode protrusion including a base end and a tip connected to the base end, and constructed of conductive rubber, wherein each of the base end and the tip contain conductive particles, and wherein an amount of the conductive particles contained in the base end is greater than an amount of the conductive particles contained in the tip such that the conductive rubber of the base end is harder than conductive rubber of the tip.

2. The bioelectrode according to claim 1, wherein, at an interface between the base end and the tip, one of the base end and the tip is provided with a protrusion, and the other of the base end and the tip is provided with a recess, and the protrusion is adapted to fit in the recess.

3. The bioelectrode according to claim 2, wherein the protrusion is provided on the base end, and the protrusion is buried in the tip.

4. The bioelectrode according to claim 2, wherein a rear end of the tip is convex, and the rear end is adapted to be buried, as the protrusion, in the base end.

5. The bioelectrode according to claim 1, including a supported section that has an electrode formation surface, wherein the electrode protrusion comprises a plurality of electrode protrusions being placed on the electrode formation surface so as to surround a placement central point provided at a center of the electrode formation surface, each of the plurality of electrode protrusions has an oblique conical shape with a rounded distal end, in the case where a normal of the electrode formation surface passing through the placement central point is defined as a main central axis, and a direction perpendicular to the main central axis is defined as a radial direction, each of the electrode protrusions is inclined relative to the main central axis such that the tip opens radially outward.

6. The bioelectrode according to claim 1, wherein a total amount of binder contained in each of the conductive rubber at the tip and the conductive rubber at the base end is 100 parts by weight, a total amount of the conductive particles contained in the conductive rubber at the tip is R1 parts by weight, a total amount of the conductive particles contained in the conductive rubber at the base end is R2 parts by weight, and 300 (parts by weight)≤R1<R2≤400 (parts by weight) is satisfied.

* * * * *